(12) United States Patent
Roswech et al.

(10) Patent No.: US 10,427,928 B2
(45) Date of Patent: Oct. 1, 2019

(54) FLUID INTERFACE TO RECEIVE REMOVABLE CONTAINER

(71) Applicant: LIFE TECHNOLOGIES CORPORATION, Carlsbad, CA (US)

(72) Inventors: Todd Roswech, Westbrook, CT (US); Jonathan Schultz, Guilford, CT (US); Chun Ho, East Haven, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 319 days.

(21) Appl. No.: 15/259,245

(22) Filed: Sep. 8, 2016

(65) Prior Publication Data

US 2017/0066642 A1 Mar. 9, 2017

Related U.S. Application Data

(60) Provisional application No. 62/216,098, filed on Sep. 9, 2015.

(51) Int. Cl.
| | | |
|---|---|---|
| *B67D 7/76* | (2010.01) | |
| *B01L 3/00* | (2006.01) | |
| *B67D 7/02* | (2010.01) | |
| *G01N 35/10* | (2006.01) | |

(52) U.S. Cl.
CPC ............ *B67D 7/0266* (2013.01); *B01L 3/502* (2013.01); *B01L 3/523* (2013.01); *B67D 7/0288* (2013.01); *B67D 7/76* (2013.01); *B01L 3/563* (2013.01); *B01L 2200/026* (2013.01); *B01L 2200/0684* (2013.01); *B01L 2200/0689* (2013.01); *B01L 2300/043* (2013.01);
(Continued)

(58) Field of Classification Search
CPC ............... B67D 7/0266; B67D 7/0288; B67D 2210/0001; B01L 3/523; B01L 3/502; B01L 2300/043; B01L 2200/0689; B01L 2200/0684; B01L 3/563; B01L 2200/026; G01N 35/1002
See application file for complete search history.

(56) References Cited

U.S. PATENT DOCUMENTS

| | | | |
|---|---|---|---|
| 5,248,056 A | 9/1993 | Shaw | |
| 6,375,315 B1 * | 4/2002 | Steinmetz | ............ B41J 2/17503 347/85 |
| 2004/0158207 A1 | 8/2004 | Hunn et al. | |

(Continued)

FOREIGN PATENT DOCUMENTS

| | | |
|---|---|---|
| EP | 0546832 | 6/1993 |
| EP | 2746736 | 6/2014 |

OTHER PUBLICATIONS

PCT/US2016/050631, International Preliminary Report on Patentability, dated Mar. 22, 2018, 1-6.
(Continued)

*Primary Examiner* — Jason K Niesz

(57) ABSTRACT

A fluidic interconnect includes a first interface including a liquid port, a gas port, and a cradle; a second interface including a liquid port, a gas port, and a swing bar to engage the cradle, a weight of a container attached to one of the first or second interfaces to drive the liquid port of the first interface into connection with the liquid port of the second interface and the gas port of the first interface into connection with the gas port of the second interface.

14 Claims, 5 Drawing Sheets

(52) U.S. Cl.
CPC ............. *B01L 2400/0487* (2013.01); *B67D 2210/0001* (2013.01); *G01N 35/1002* (2013.01)

(56) References Cited

U.S. PATENT DOCUMENTS

| | | |
|---|---|---|
| 2005/0168540 A1 | 8/2005 | Wilson et al. |
| 2006/0169719 A1 | 8/2006 | Bul |
| 2009/0246085 A1 | 10/2009 | Watson et al. |
| 2010/0324487 A1 | 12/2010 | Lynch et al. |

OTHER PUBLICATIONS

PCT/US2016/050631, International Search Report and Written Opinion, dated Dec. 5, 2016, 1-12.

* cited by examiner

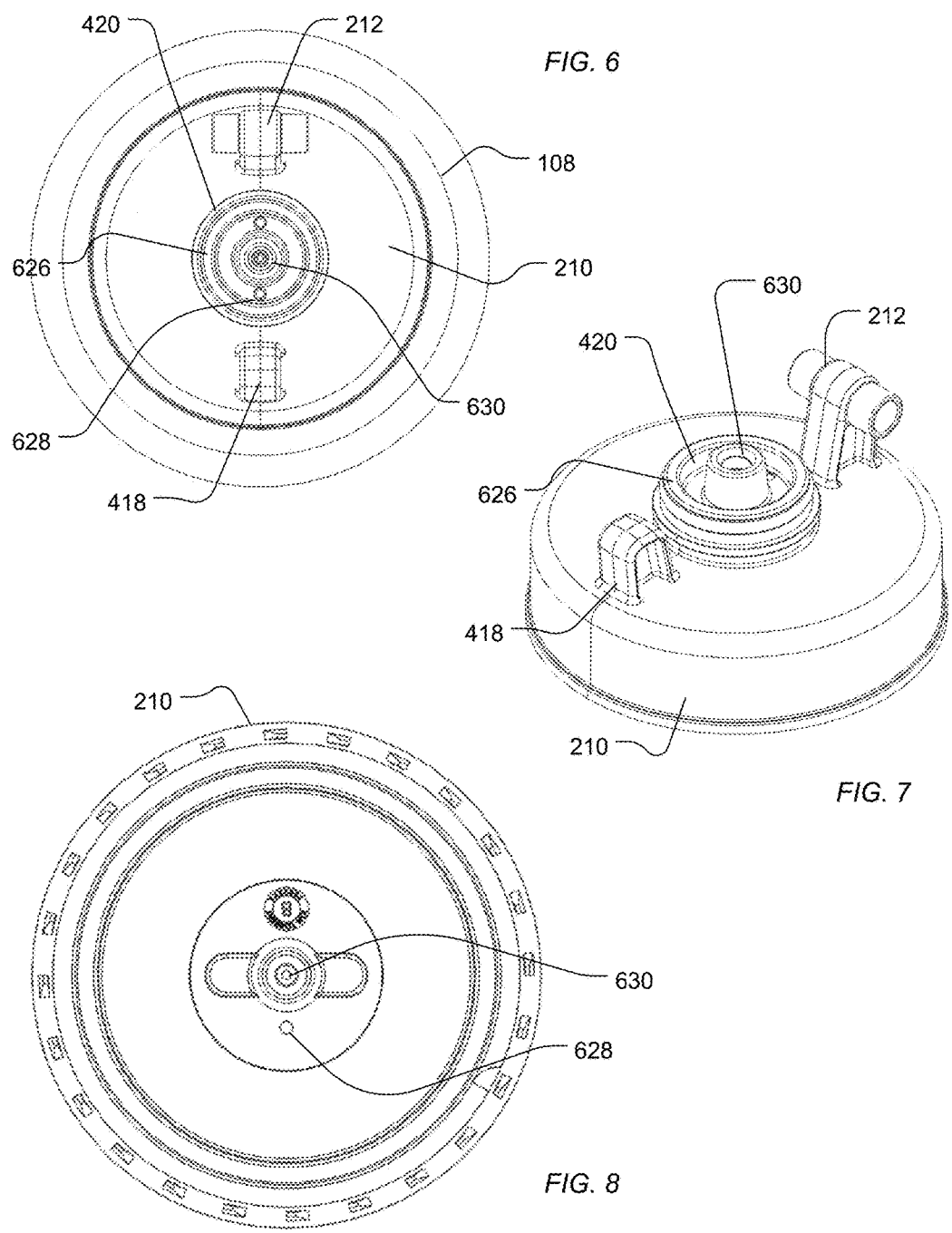

FLUID INTERFACE TO RECEIVE REMOVABLE CONTAINER

CROSS-REFERENCE TO RELATED APPLICATION(S)

This application claims benefit of U.S. Provisional Application No. 62/216,098, filed Sep. 9, 2015, which is incorporated herein by reference in its entirety.

FIELD OF THE DISCLOSURE

This disclosure, in general, relates to containers for liquid media and interfaces for attaching such containers to instruments.

BACKGROUND

Increasingly, laboratories are seeking instruments to perform testing of analytes. Preparation of such instruments can be labor-intensive, relying on the time-consuming preparation of reagent solutions. To reduce preparation times, industry is turning to pre-made reagent solutions provided to laboratory customers in kits. But, the shipping and handling of liquid reagents can lead to degradation of the reagent and spillage. As such, an improved reagent container and instrument interface would be desirable.

SUMMARY

In a first aspect, a fluidic interconnect includes a first interface including a liquid port, a gas port, and a cradle; a second interface including a liquid port, a gas port, and a swing bar to engage the cradle, a weight of a container attached to one of the first or second interfaces to drive the liquid port of the first interface into connection with the liquid port of the second interface and the gas port of the first interface into connection with the gas port of the second interface.

In a second aspect, a system includes an instrument including a panel and a first interface to engage a container, the first interface including a liquid port, a gas port, and a cradle, the cradle disposed further from the panel than the liquid port; and a container including a second interface including a liquid port, a gas port, and a swing bar to engage the cradle, the container to swing toward the panel around a pivot formed when the swing bar engages the cradle to connect the liquid port of the first interface to the liquid port of the second interface and the gas port of the first interface to the gas port of the second interface.

In a third aspect, a method of connecting a container to an instrument includes applying a swing bar of a container to a cradle of an instrument interface, wherein the instrument includes a panel and the instrument interface to engage the container, the instrument interface including a liquid port, a gas port, and the cradle, the cradle disposed further from the panel than the liquid port of the instrument interface; the container including a container interface including a liquid port, a gas port, and the swing bar to engage the cradle, the container to swing toward the panel around a pivot formed when the swing bar engages the cradle to connect the liquid port of the instrument interface to the liquid port of the container interface and the gas port of the instrument interface to the gas port of the container interface. The method further includes applying gas through the gas port to drive liquid from container through the liquid ports into the instrument.

BRIEF DESCRIPTION OF THE DRAWINGS

The present disclosure may be better understood, and its numerous features and advantages made apparent to those skilled in the art by referencing the accompanying drawings.

FIG. 5, FIG. 6, FIG. 7, and FIG. 8 include illustrations of an exemplary top of a container.

The use of the same reference symbols in different drawings indicates similar or identical items.

DETAILED DESCRIPTION

In an exemplary embodiment, an instrument includes a fluidics interface to receive a removable container. The instrument side interface can include ports, such as a liquid port or a gas port. The removable container can include complementary ports, such as a liquid port and a gas port. In a particular example, a top of the container includes a swing bar to couple with a cradle of the instrument side fluidics interface. Once the swing bar and cradle are engaged, the container can swing into place to engage the fluidics interface of the instrument. In a particular example, the cradle is positioned outward from the instrument relative to the fluidics ports.

Figure 1:
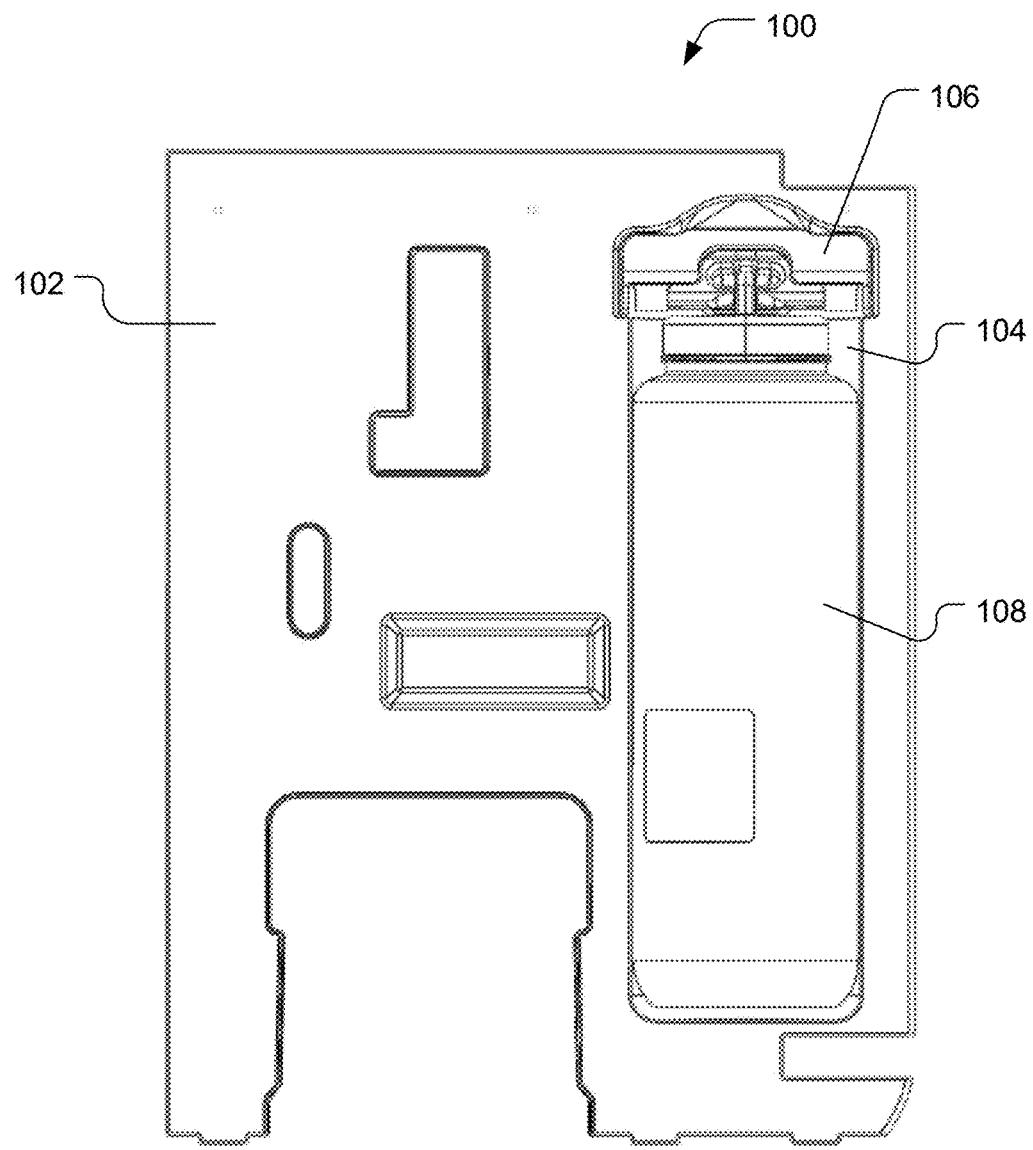
FIG. 1 includes an illustration of an exemplary instrument panel for receiving a container.

In an example illustrated in FIG. 1, an instrument 100 can include a panel 102 having a recess 104 to receive a container 108. The container 108 can have a top configured to engage a fluidics interface 106 of the instrument 100.

Figures 2, 3:
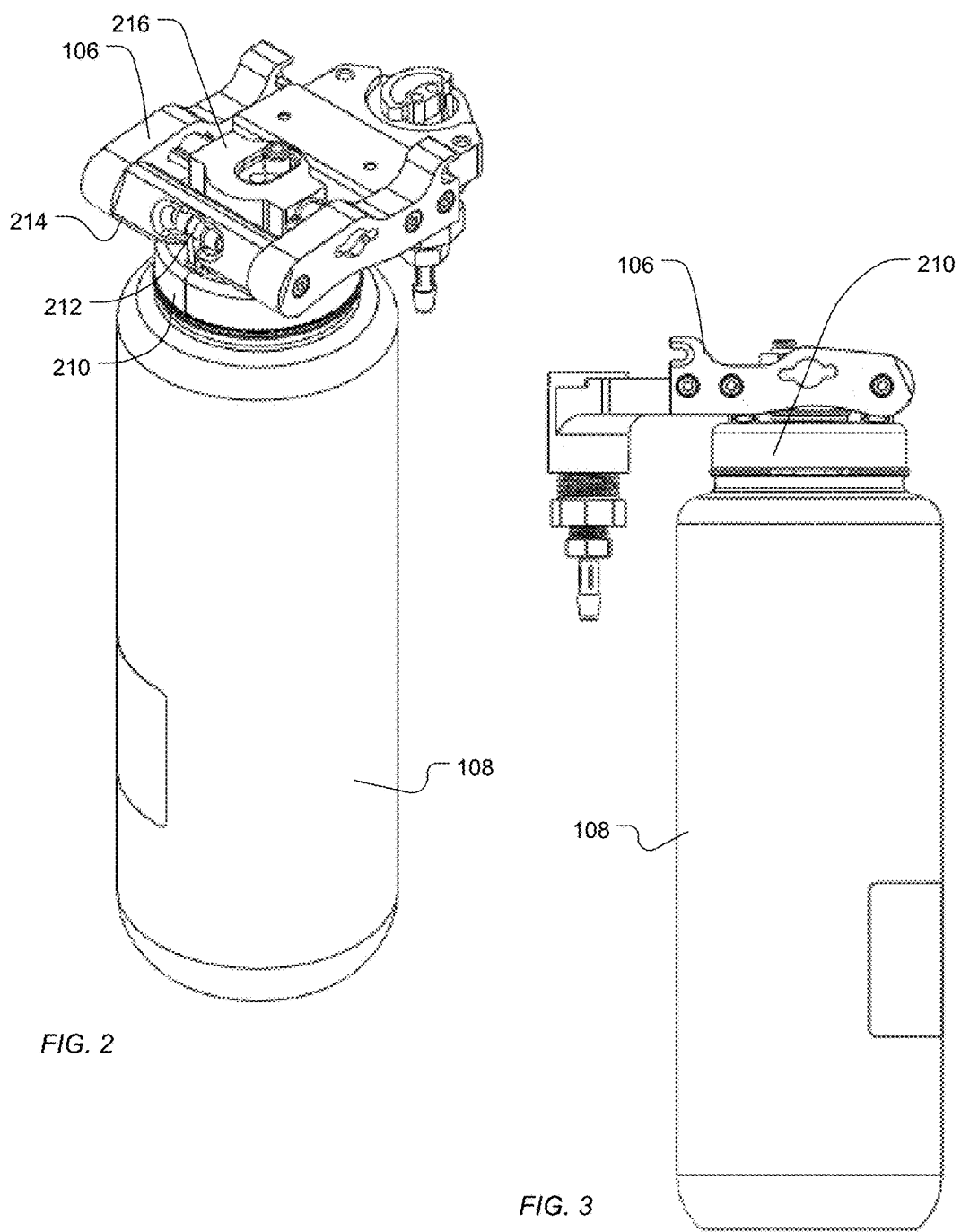
FIG. 2 and FIG. 3 include illustrations of an exemplary container and instrument interface.

For example, as illustrated in FIG. 2 and FIG. 3, the fluidics interface 106 can engage a top 210 of the container 108. In particular, a swing bar 212 of the top 210 of the container 108 can engage a cradle 214 of the fluidics interface 106. The container 108 can swing into place, engaging fluid manifold 216 of the fluidics interface 106 of the instrument.

Figure 4:
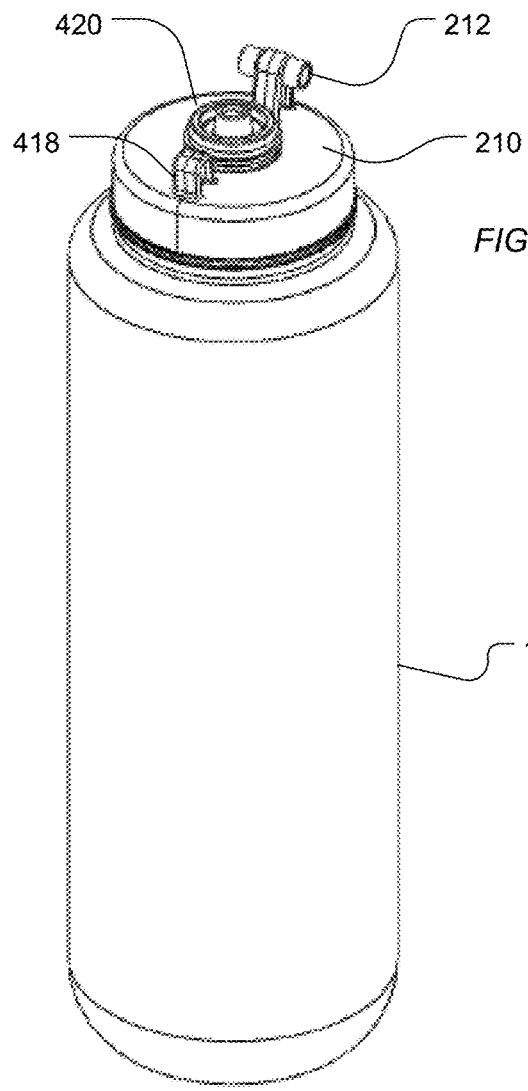
FIG. 4 includes an illustration of exemplary container.

In a particular example illustrated in FIG. 4, the container 108 can include a top 210 having a fluidics interface 420. As illustrated, the fluidics interface 420 is axially centrally located along an axis of the container 108 and top 210. To one side of the fluidics interface 420 on the top 210 is positioned a swing bar 212, which can form part of the top 210. Optionally, opposite the swing bar 212 relative to the fluidics interface 420 is a counter structure 418.

Figure 5:
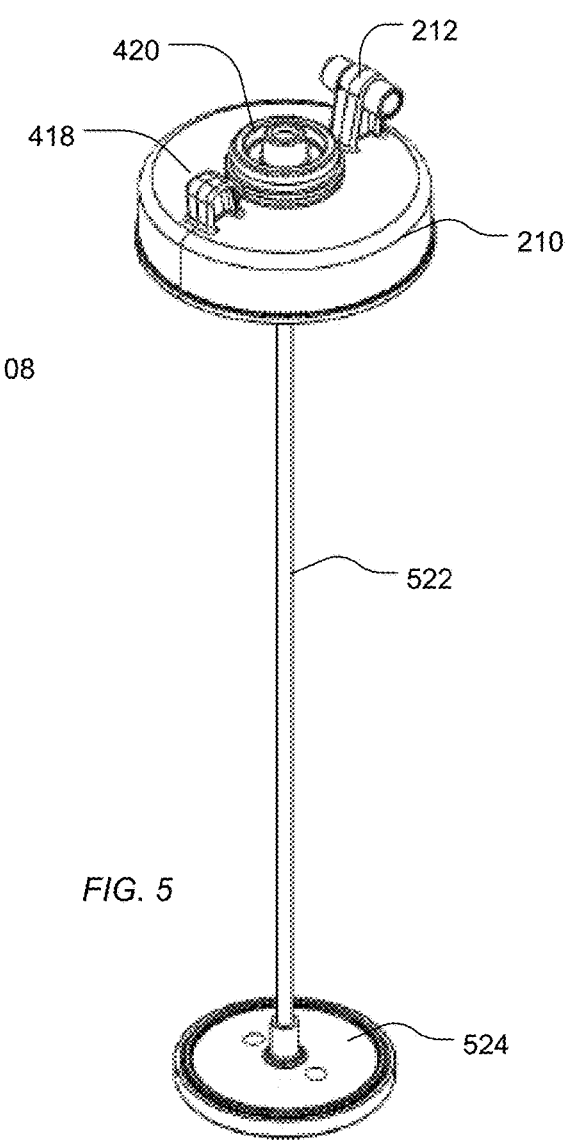

Optionally, the top 210 of the container 108 can be connected to a sipper 522 residing within the container 108, as illustrated in FIG. 5. At a distal end of the sipper 522, a filter 524 can be attached. In a particular example in which the container 108 is to store a reagent including solids chemistry, such as solid-state buffers, the reagent solution can be drawn through the filter 524 and sipper 522 and out of the fluidics interface 420.

As illustrated in more detail in FIG. 6, FIG. 7, and FIG. 8, the top 210 of the container 108 includes the fluidics port 420 centrally located along an axis of the container 108, and optionally concentric with the top 210. When viewed from above, as illustrated in FIG. 6, the swing bar 212 is disposed on an opposite side of the fluidics port 420 from a counter structure 418. For example, a line can extend across the upper surface of the top 210 through the center of the swing bar 212, the fluidics port 420, and the counter structure 418.

As illustrated in FIG. 6 and FIG. 7, the fluid interface 420 can include a peripheral sealing ring 626. A liquid port 630 comprising a raised sealing structure can be disposed at an axial center of the fluidics interface 420. In an example, a gas port 628 can be disposed to a side of the liquid port 630 and within the boundary of the sealing ring 626. As illustrated in FIG. 8, an underside of the top can include the fluidics port 630 centrally located and an opening to the gas port 628.

Such a configuration of the top 210 of the container 108 and the associated liquid and gas ports can effectively receive a complementary lid during shipping. Such a configuration can limit fluid leakage.

Figure 9:
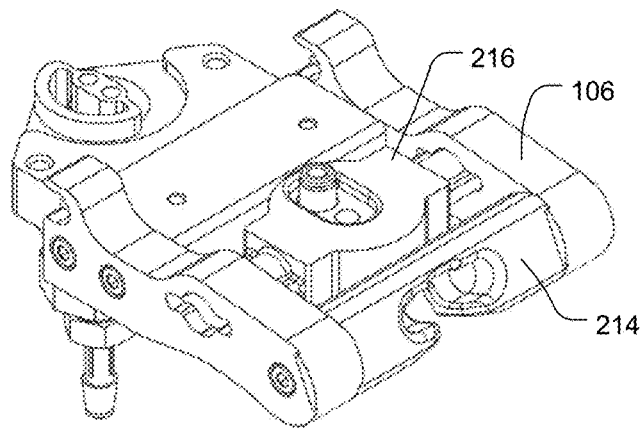
FIG. 9, FIG. 10, and FIG. 11 include illustrations of exemplary instrument side fluidics interfaces.
Figure 10:
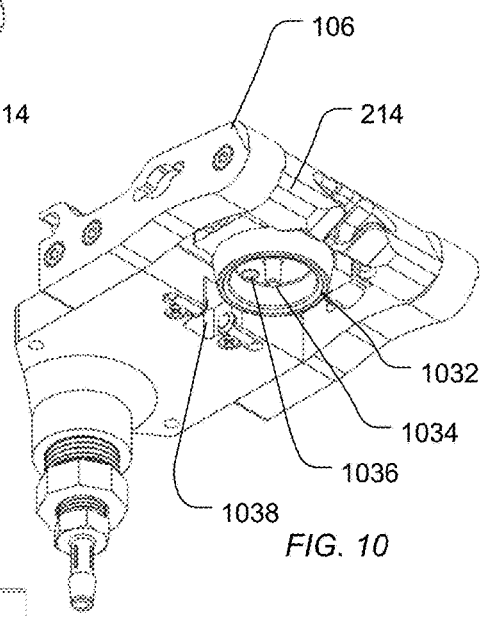
Figure 11:
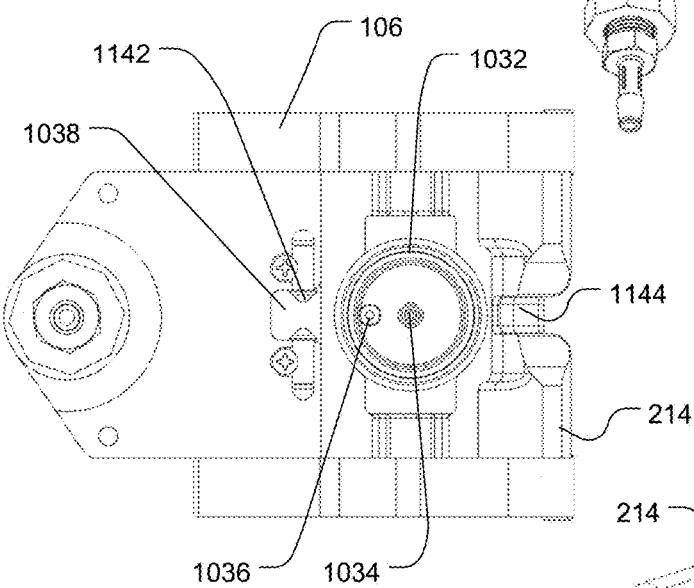

FIG. 9, FIG. 10, and FIG. 11 include illustrations of an exemplary instrument side fluidics interface 106. The fluidics interface 106 includes a cradle 214 and a fluidics port 216. In particular, the cradle 214 is disposed further from the instrument panel than the fluidics port 216.

As illustrated in FIG. 10, the fluidics interface 106, when viewed from an underside, includes a sealing structure 1032 to engage the sealing ring 626 of the container 108. In an example, a liquid port 1034 extends and can engage or enter the liquid port 630 of the container 108. Alternatively, the liquid port 630 of the container can enter the liquid port 1034 of the fluidics interface 106. Optionally, a gas port 1036 can be provided to access the gas port 628 of the container 108 by virtue of the seals formed between the rings 1032 and 626, as well as the seal formed by the liquid ports 1034 and 630.

As further illustrated in FIG. 10, the fluidics interface 106 can include a recess 1038 to receive the counter structure 418 of the top 210 of the container 108. As illustrated in FIG. 11, connectors 1142 can be positioned on one or both sides of the recess 1038 and can releasably secure the counter structure 418 in place.

Figure 12:
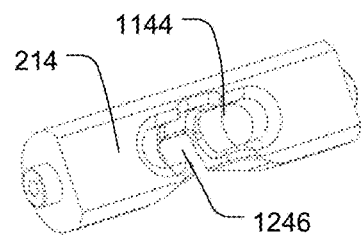
FIG. 12 includes an illustration of an exemplary cradle portion of an instrument side fluidics interface.

As further illustrated in FIG. 11, the cradle 214 includes a recess 1144 to receive the swing bar 212. For example, as illustrated in FIG. 12, the cradle 214 includes a recess 1144 and a slot 1246 to receive the swing bar 212 of the container 108 and allow the container 108 to swing towards the instrument and engage the connectors 1142 and the fluidics ports 1034 and 1036.

In use, the swing bar 212 of the top 210 of the container 108 can engage the cradle 214 of the fluidics interface 106 at an angle. The container 108 can then swing along around a pivot formed by the cradle 214 and swing bar 212 into the recess 104 of the instrument 100. The counter structure 418 can engage the recess 1038 and optional connectors 1142. In a particular example, the weight of the bottle and optional connection to the connectors 1142 forms a leak-tight seal between the fluidics ports 420 of the container 108 and the fluid manifold of the fluidics interface 106. Optionally, air can be applied through the gas ports and into the container 108. The liquid reagent solution within the container can be drawn or pushed through the liquid port 630 and into the instrument 100. To disengage the container 108, the process can be reversed.

While the examples illustrated herein include a cradle in the instrument side fluidics interface and a swing bar on the top of the container, the container can alternatively include the cradle and the instrument side fluidics interface the swing bar. In another alternative example, the positioning of the liquid port and the gas port can be reversed or can be disposed in different positions with different male or female configurations.

In a first aspect, a fluidic interconnect includes a first interface including a liquid port, a gas port, and a cradle; a second interface including a liquid port, a gas port, and a swing bar to engage the cradle, a weight of a container attached to one of the first or second interfaces to drive the liquid port of the first interface into connection with the liquid port of the second interface and the gas port of the first interface into connection with the gas port of the second interface.

In an example of the first aspect, the first interface is coupled to an instrument and the second interface is coupled to the container. For example, the cradle and swing bar engage further from the instrument than the liquid and gas ports.

In another example of the first aspect and the above examples, the container further includes a sipper internal to the container and attached to the liquid port of the container. For example, the fluidic interconnect further includes a filter attached to an end of the sipper distal from the liquid port of the container.

In a further example of the first aspect and the above examples, the gas port of the first or second interface of the container is to receive gas from the gas port of the first or second interface coupled to an instrument.

In an additional example of the first aspect and the above examples, the liquid port of the second interface is centrally axial disposed within a sealing ring. For example, the gas port of the second interface is disposed between the liquid port and the sealing ring.

In another example of the first aspect and the above examples, the second interface further includes a counter structure and the first interface includes a recess to receive the counter structure. For example, the counter structure is disposed adjacent the liquid port on an opposite side of the liquid port from the swing bar.

In a second aspect, a system includes an instrument including a panel and a first interface to engage a container, the first interface including a liquid port, a gas port, and a cradle, the cradle disposed further from the panel than the liquid port; and a container including a second interface including a liquid port, a gas port, and a swing bar to engage the cradle, the container to swing toward the panel around a pivot formed when the swing bar engages the cradle to connect the liquid port of the first interface to the liquid port of the second interface and the gas port of the first interface to the gas port of the second interface.

In an example of the second aspect, the container further includes a sipper internal to the container and attached to the liquid port of the second interface. For example, the system further includes a filter attached to an end of the sipper distal from the liquid port of the container.

In another example of the second aspect and the above examples, the liquid port of the second interface is centrally axial disposed within a sealing ring. For example, the gas port of the second interface is disposed between the liquid port and the sealing ring.

In a further example of the second aspect and the above examples, the second interface further includes a counter structure and the first interface includes a recess to receive the counter structure. For example, the counter structure is disposed adjacent the liquid port on an opposite side of the liquid port from the swing bar.

In a third aspect, a method of connecting a container to an instrument includes applying a swing bar of a container to a cradle of an instrument interface, wherein the instrument includes a panel and the instrument interface to engage the container, the instrument interface including a liquid port, a gas port, and the cradle, the cradle disposed further from the panel than the liquid port of the instrument interface; the container including a container interface including a liquid port, a gas port, and the swing bar to engage the cradle, the container to swing toward the panel around a pivot formed when the swing bar engages the cradle to connect the liquid port of the instrument interface to the liquid port of the container interface and the gas port of the instrument interface to the gas port of the container interface. The method further includes applying gas through the gas port to drive liquid from container through the liquid ports into the instrument.

In an example of the third aspect, the method further includes swinging the container into a recess of the panel to engage connectors of the instrument interface to a counter structure of the container interface.

In another example of the third aspect and the above examples, the container further includes a filter in fluid communication with the liquid port of the container interface, the method further including filtering a liquid within the container.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A fluidic interconnect comprising:
    a first interface including a liquid port, a gas port, and a cradle;
    a second interface including a liquid port, a gas port, and a swing bar to engage the cradle, a weight of a container attached to one of the first or second interfaces to drive the liquid port of the first interface into connection with the liquid port of the second interface and the gas port of the first interface into connection with the gas port of the second interface;
    wherein the first interface is coupled to an instrument and the second interface is coupled to the container, the cradle and swing bar engaging further from the instrument than the liquid and gas ports.

2. The fluidic interconnect of claim 1, wherein the container further includes a sipper internal to the container and attached to the liquid port of the container.

3. The fluidic interconnect of claim 2, further comprising a filter attached to an end of the sipper distal from the liquid port of the container.

4. The fluidic interconnect of claim 1, wherein the gas port of the first or second interface of the container is to receive gas from the gas port of the first or second interface coupled to an instrument.

5. The fluidic interconnect of claim 1, wherein the liquid port of the second interface is centrally axial disposed within a sealing ring.

6. The fluidic interconnect of claim 5, wherein the gas port of the second interface is disposed between the liquid port and the sealing ring.

7. The fluidic interconnect of claim 1, wherein the second interface further includes a counter structure and the first interface includes a recess to receive the counter structure.

8. The fluidic interconnect of claim 7, wherein the counter structure is disposed adjacent the liquid port on an opposite side of the liquid port from the swing bar.

9. A system comprising:
    an instrument including a panel and a first interface to engage a container, the first interface including a liquid port, a gas port, and a cradle, the cradle disposed further from the panel than the liquid port;
    a container including a second interface including a liquid port, a gas port, and a swing bar to engage the cradle, the container to swing toward the panel around a pivot formed when the swing bar engages the cradle to connect the liquid port of the first interface to the liquid port of the second interface and the gas port of the first interface to the gas port of the second interface, wherein the liquid port of the second interface is central-axially disposed within a sealing ring.

10. The system of claim 9, wherein the container further includes a sipper internal to the container and attached to the liquid port of the second interface.

11. The system of claim 10, further comprising a filter attached to an end of the sipper distal from the liquid port of the container.

12. The system of claim 9, wherein the gas port of the second interface is disposed between the liquid port and the sealing ring.

13. The system of claim 9, wherein the second interface further includes a counter structure and the first interface includes a recess to receive the counter structure.

14. The system of claim 13, wherein the counter structure is disposed adjacent the liquid port on an opposite side of the liquid port from the swing bar.

* * * * *